United States Patent [19]

Nagashima et al.

[11] 4,378,492
[45] Mar. 29, 1983

[54] LASER OUTPUT MEASURING DEVICE FOR LASER KNIFE

[75] Inventors: Hironobu Nagashima, Fukuoka; Teruo Sakai, Warabi; Yuzo Noguchi, Kawagoe; Kiyoshi Itoh, Fukuoka, all of Japan

[73] Assignee: Asahi Kogaku Kogyo Kabushiki Kaisha, Tokyo, Japan

[21] Appl. No.: 233,710

[22] Filed: Feb. 12, 1981

[30] Foreign Application Priority Data

Feb. 15, 1980 [JP] Japan ................................. 55-17396

[51] Int. Cl.$^3$ .............................................. H01J 40/14
[52] U.S. Cl. ..................................... 250/215; 356/226
[58] Field of Search .......................... 250/215, 214 R; 356/218, 226, 229

[56] References Cited

U.S. PATENT DOCUMENTS 4,288,161  9/1981  Fortescue ............................. 356/226

*Primary Examiner*—David C. Nelms
*Attorney, Agent, or Firm*—Sughrue, Mion, Zinn, Macpeak and Seas

[57] ABSTRACT

A laser output measuring device for a laser knife having a flexible manipulator in which the output power at the operating end of the manipulator is accurately displayed at all times independent of changes in the transmissivity of the manipulator. A measuring hole member is provided in a housing in which is positioned a laser oscillator, a shutter device and a power detecting device. When the end of the manipulator is inserted in the measuring hole member, the shutter is positioned such that the output laser beam is directed onto the power detecting unit while when the end of the manipulator is free, the position of the shutter is determined by a foot switch such that the output laser beam from the laser oscillator can either be directed into the manipulator or to the power detecting unit. An arithmetic circuit is provided which measures the output power at the end of the manipulator when the end of the manipulator is positioned in the measuring hole member and which scales the output power measured when the end of the manipulator is free and the output beam of the laser oscillator is directed by the shutter to the power detecting unit such that the measured power always corresponds accurately to the output power at the end of the manipulator.

8 Claims, 5 Drawing Figures

LASER OUTPUT MEASURING DEVICE FOR LASER KNIFE

BACKGROUND OF THE INVENTION

The present invention relates to a device for measuring and displaying laser outputs for a laser knife.

In almost all conventional laser knives, a power meter is provided in the housing of the laser oscillator of the device so that the laser output at the emergence port of the laser oscillator is measured by the power meter and is displayed by a meter on the panel of the laser source housing.

In general, a laser beam is introduced to the end of the operating section of a laser knife, namely, the handpiece, through a flexible optical conduction device called a manipulator whereby the laser beam is applied as a minute optical spot to the part of the body to be operated upon. In general, seven reflecting mirrors are provided in the articulation section of a manipulator and a focusing lens is provided in the handpiece. The power of the laser beam is attenuated by the these reflecting mirrors in accordance with their reflection factors and the focusing lens in accordance with its transmission factor. For instance in the case where the reflection factor and the transmission factor are both 97%, a laser power of 30 W at the emergence port of the laser oscillator is reduced to 23.5 W at the emergence terminal of the handpiece.

The laser knife operator should confirm the laser power before the surgical operation. The laser power which should be confirmed by the operator is not that at the emergence port of the laser oscillator but that at the emergence port of the manipulator. It is true that the laser knife is so designed that the operator can readily increase or decrease the laser power and the laser irradiation time according to the conditions of the body part to be operated; however, in a conventional laser power measuring technique, it is impossible for the operator to directly know the irradiation laser power.

A drawback accompanying the conventional laser power measuring method is that the reflection factors of the above-described reflecting mirrors are not uniform and moreover they change with time. Accordingly, the ratio of the laser power at the emergence port of the laser oscillator to the laser power at the emergence port of the manipulator is not always constant. The reason why the reflection factors change with time is that dust falling on the reflecting mirrors becomes firmly attached to the vacuum-evaporated films on the mirror surfaces by the laser beams thereby decreasing their reflection factors. On the other hand, the transmission factor of the focusing lens is also reduced for the same reason and also due to contamination by carbonized tissue produced during operations.

In addition, it is well known in the art that, as a laser oscillation mode can be changed from a single mode to a multi-mode by thermal or mechanical deformation of the laser oscillator, the ratio of the laser power at the output port of the laser oscillator to the laser power at the output port of the manipulator has a tendency to change.

Laser knife manufacturer commonly use commercially available portable laser power meters to measure the laser power at the end of the manipulator during manufacture and test. However, it is not suitable for technical and security reasons for the user to perform such measurements during a surgical operation.

SUMMARY OF THE INVENTION

In view of the foregoing, the invention provides devices with which an operator can read the laser power at the end of the manipulator at all times merely by carrying out a simple power measuring operation before starting a surgical operation.

More specifically, the invention provides a laser power meter with which, firstly, the operator can read the laser power at the end of the manipulator merely by performing a simple power measuring operation while preparing for a surgical operation. Also, the operator can read the laser power during a surgical operation if desired.

A laser power meter includes a power detecting unit provided in the housing of a laser oscillator at the emergence port of the latter, a shutter device disposed in front of the detecting unit for selectively intercepting the laser beam, a measuring hole member into which the end section of the manipulator is fixedly inserted, an optical conduction detecting sensor for detecting the insertion of the manipulator into the measuring hole member, an arithmetic circuit for converting the laser power at the output terminal of the laser oscillator into the laser power at the end section of the manipulator, and a display unit for displaying the laser power.

When the end section of the manipulator is inserted into the measuring hole member and is fixedly secured thereto by the operator before a surgical operation, the shutter device is opened so that the power of the laser beam from the end section is detected by the power detecting unit and with the results stored in a memory through the arithmetic circuit. Thereafter, upon removal of the end section of the manipulator from the measuring hole member, the shutter device is closed to allow the laser beam from the laser oscillator to reach the power detecting unit. The ratio of the laser powers with respect to these two positions is stored and calculated by the arithematic circuit system and the laser power at the end section of the manipulator is accordingly displayed on the display unit at all times. In the case where it is required to read the laser power during the surgical operation, the laser power displayed on the display unit is that at the end section of the manipulator although the laser beam from the laser oscillator is applied to the power detecting unit.

DESCRIPTION OF THE PREFERRED EMBODIMENTS

The present invention will be explained by a detailed description of its preferred embodiment with reference to the accompanying drawings.

Figure 1:
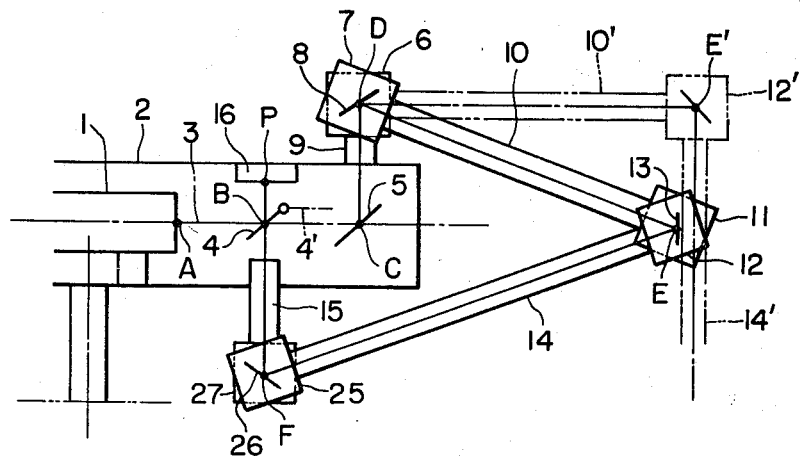
FIG. 1 is an explanatory diagram showing the arrangement of various components of a laser output meter according to the invention.

FIG. 1 is an explanatory diagram for a description of the arrangement of various components of a laser power meter according to the invention and a method of measuring laser power with the meter. A laser oscillator 1, a shutter plate 4, a first mirror 5 and a power detecting unit 16 are arranged in a housing, as shown in FIG. 1. A manipulator made up of articulations 6, 7, 11, 12, 25 and 27 and arms 9, 10, 14 and 15 connecting these articulations is flexibly constructed. In operating the laser knife, the shutter plate 4 is positioned at indicated by 4' to direct the laser beam 3 to the first mirror 5 while the arms 10 and 14 of the manipulator are positioned as indicated by 10' and 14'. That is, the arms are positioned substantially horizontal and vertical, respectively, so that the operator can hold the handpiece (not shown) at the end of the manipulator for the operation.

Before measurement of the laser output at the end of the manipulator, the end section 15 is inserted into a measuring hole member provided in the housing 2 as shown in FIG. 1. That is, in this case, the horizontal arm 10 and the vertical arm 14 of the manipulator are positioned as indicated by the solid lines in FIG. 1 so that the laser beam 3 advances in the order of A, B, C, D, E, F and P to reach the power detecting unit 16. When the end section 15 of the manipulator is removed from measuring hole member, the shutter plate 4 is closed to allow the laser beam 3 to advance along the optical path A-B-P to reach the power detecting unit 16. In practice, the power detecting unit 16 can be a thermocouple type detector, for instance.

Figure 2:
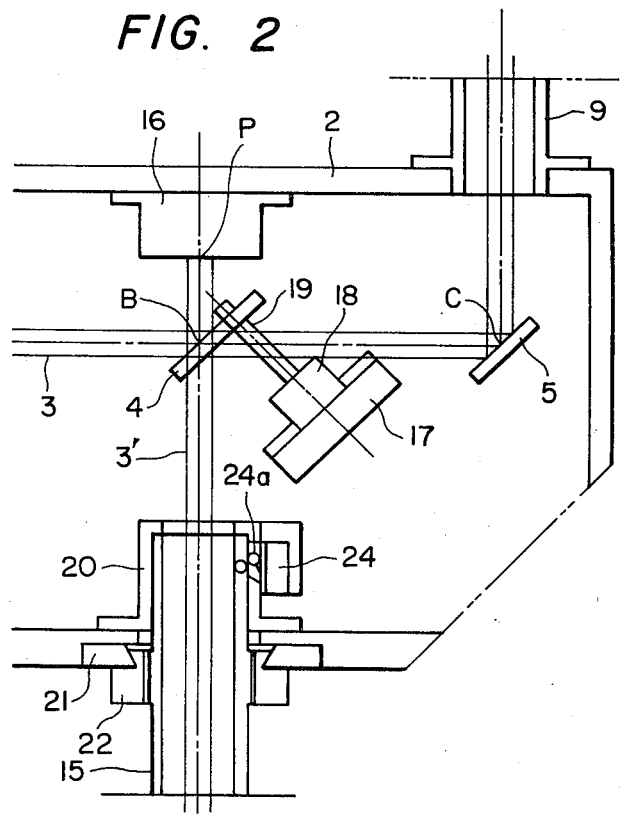
FIG. 2 is an explanatory diagram showing a measuring hole member and a shutter device in FIG. 1 in detail.
Figure 3:
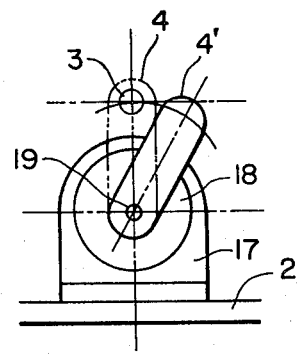
FIG. 3 is a diagram showing the shutter device as viewed along the axis of the laser beam.

FIG. 2 is an explanatory diagram showing the measuring hole member and the shutter device in more detail. FIG. 3 is a diagram showing the shutter device as viewed along the optical axis of the laser beam. The end section 15 of the manipulator, after being inserted into the measuring hole member 20, which is fixedly secured to the housing 2, is secured to the measuring hole member 20 by tightening a nut 22. In FIG. 2, reference numeral 21 designates a retaining member provided to prevent the nut 22 from coming off. In the inserted position, the actuator 24a of an optical conduction detecting sensor 24 provided in the measuring hole member 20 is operated to provide an output signal in response to which the shutter plate 4 of the shutter device is opened so that the laser beam 3' from the manipulator end section 15 falls on the power detecting unit 16.

The operation of the shutter device is illustrated in FIG. 3. A rotary solenoid 18 is fixedly mounted on a holder 17 which is secured to the housing 2 and the shutter plate 4 is fastened to the end of the shaft 19 of the rotary solenoid 18. When the rotary solenoid 18 is deenergized, the shutter plate 4 is positioned as indicated at 4 to intercept the laser beam 3. When the sensor 24 is operated as described above, the shutter plate 4 is turned to a position indicated by 4' in response to the output signal to allow the laser beam 3 to reach the manipulator. The shutter plate 4 is made of light metal. The portion of the shutter plate 4 which is irradiated by the laser beam is coated with a total reflection film of gold or the like by vacuum evaporation so that almost all of the laser beam is reflected by the total portion of the shutter plate 4. Therefore, the temperature of the coated portion is scarcely increased by the laser beam.

As shown in FIG. 2, the nut 22 is employed to fixedly hold the end section of the manipulator. However, an end section tightening technique using a bayonet may be employed to secure the end section of the manipulator to the measuring hole member by a so-called "one-touch operation".

With respect to the shutter operation, security provisions for the laser beam will be briefly described. An ordinary surgical operation and a power measurement will be referred to as "an irradiation mode" and "a measurement mode", respectively. For security, a switch for switching between these two modes is provided on the front panel of the laser source housing. In the irradiation mode, the laser irradiation instruction is usually effected by operating the foot switch. When the laser beam is not generated, the shutter plate 4 is maintained closed. However, the shutter plate 4 is opened by the foot switch operation signal. When the irradiation mode is switched over to the measurement mode by operating the switch, then the irradiation instruction from the foot switch becomes ineffective. That is, the shutter plate 4 is opened by the instruction from the sensor 24. Thus, the laser beam cannot be generated without fixedly securing the end section 15 of the manipulator to the measuring hole member.

Figure 4:
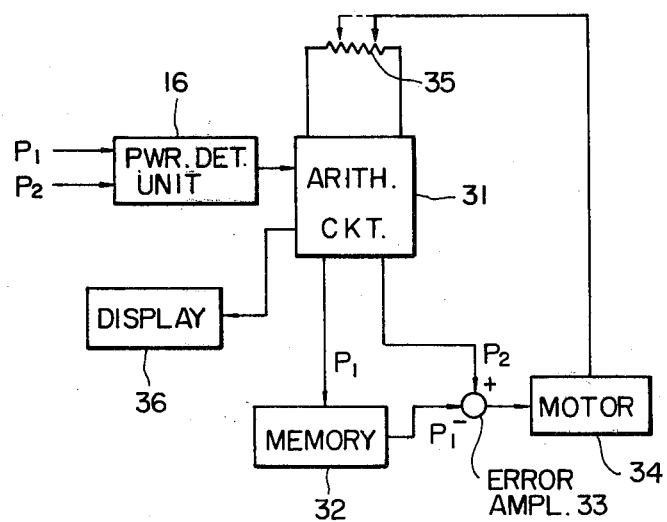
FIG. 4 is a block diagram showing an electronic circuit system of the laser output meter.

FIG. 4 shows an electronic circuit system for the laser power meter. According to the above-described operating procedure, an laser output $P_1$ at the end section of the manipulator is detected by the power detecting unit 16 and is applied through an arithmetic circuit 31 to a memory 32 where it is stored. Then, a laser output $P_2$ at the emergence terminal of the laser oscillator is applied through the arithmetic circuit 31 to an error amplifier 33 where the two laser outputs $P_1$ and $P_2$ are subjected to comparison and a difference output provided. A motor 34 is turned at a rate determined by the magnitude of the difference output thus provided. A rotary type potentiometer 35 is coupled to the motor 34. The wiper of the potentiometer 35 is moved in response to the difference output to control the gain of the arithmetic circuit 31. Thus, the laser output power at the end section of the manipulator is displayed on a display unit 36.

In FIG. 4, the electronic circuit system except for the power detecting unit 16 and the display unit 36 will be referred to as "an arithmetic system" hereinafter.

During an operation, the laser output power at the end section of the manipulator can be confirmed by depressing a power measuring button on the front panel of the laser source housing. In this case, the laser beam oscillates with the shutter plate 4 maintained closed and the laser output $P_2$ at the emergence port of the laser oscillator is detected by the power detecting unit 16. By the above-described operation of the arithmetic circuit system, the value of $P_2$ in terms of power at the end section of the manipulator is displayed on the display unit 36.

In order to detect the laser output at the end section of the manipulator, the power detecting unit in the laser housing is used. However, an additional power detecting unit may be provided on the front panel of the laser source housing for this purpose if desired. However, the provision of the additional power detecting unit suffers from the disadvantage that two detecting units of different characteristics are needed, the circuit arrangement becomes unavoidably intricate, the industrial design of the panel is difficult, and the operating functions of the panel made difficult.

Thus, preferably the two laser outputs are detected by a single power detecting unit taking advantage of the flexibility of the manipulator. This is one of the specific advantageous features of the present invention.

As is apparent from the above description, with the laser power meter according to the invention, the laser output at the emergence port of the laser oscillator and the laser output at the end section of the manipulator can be calibrated readily be the common power detecting unit before a surgical operation. Even during the surgical operation, the laser output at the end section of the manipulator can be read at all times. In addition, the laser output at the end section of the manipulator can be readily calibrated taking into account the deterioration of the reflecting mirrors of the manipulator and the variations with time of the laser oscillating mode.

The laser power meter is applicable not only to a laser knife using a $CO_2$ laser but also to laser knives using the other types of lasers and to a coagulator.

Figure 5:
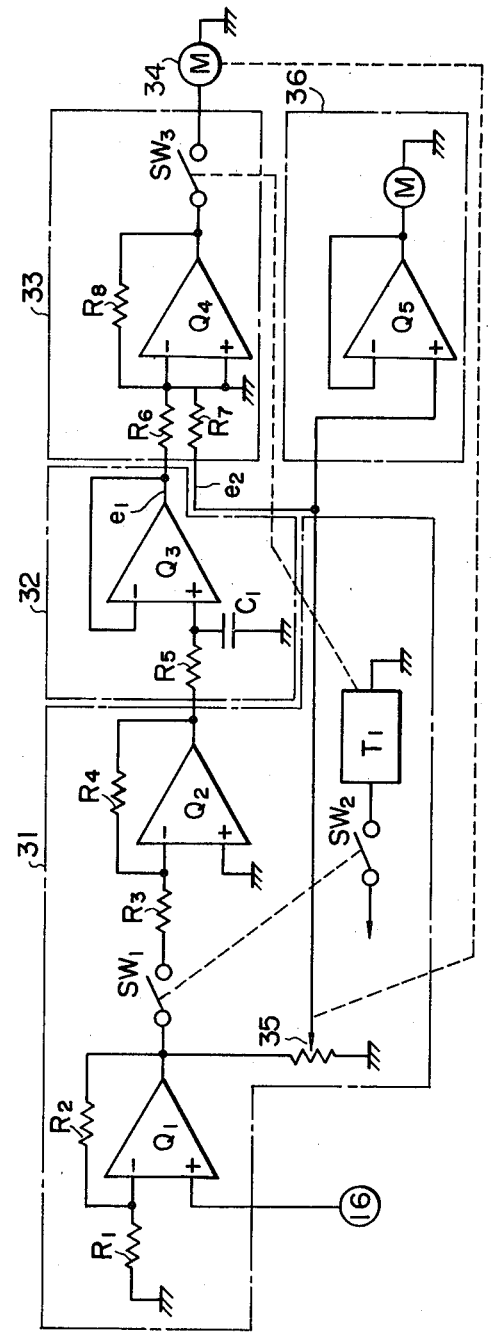
FIG. 5 is a detailed schematic diagram of the electronic circuit system of FIG. 4.

FIG. 5 shows a specific example of the circuits of FIG. 4. In FIG. 5, $Q_1$, $Q_2$, $Q_3$, $Q_4$ and $Q_5$ are operational amplifiers, $R_1$, $R_2$, $R_3$, $R_4$, $R_5$, $R_6$, $R_7$ and $R_8$ are resistors, $C_1$ is a capacitor, and $SW_1$ and $SW_2$ are contacts of the optical conduction detector sensor 24. $T_1$ is an off-timer in which, when the contact $SW_2$ is closed, a contact $SW_3$ thereof closes simultaneously therewith and after the contact $SW_2$ is opened, the contact $SW_3$ opens after a predetermined period of time.

When the end section of the manipulator is inserted into the measuring hole member 20, the contacts $SW_1$ and $SW_2$ of the sensor 24 are closed. At the same time, the laser output $P_1$ at the end section of the manipulator falls on the power detecting unit 16. A voltage output proportional to the laser output $P_1$ is applied to the operational amplifier $Q_1$, amplified therein, and then applied through the contact $SW_1$ and resistor $R_3$ to the operational amplifier $Q_2$. However, with $R_3=R_4$, the output obtained from the operational amplifier $Q_1$ is only inverted by the operational amplifier $Q_2$. It is then applied to the resistor $R_5$. The output obtained from the operational amplifier $Q_2$ passes through the resistor $R_5$ and is stored by the capacitor $C_1$. A voltage $e_1$ equal to the stored voltage on the capacitor $C_1$ is applied through the resistor $R_6$ to the operational amplifier $Q_4$.

When the end section of the manipulator is removed from the measuring hole member 20, the contacts $SW_1$ and $SW_2$ of the sensor 24 are opened. At this time, the laser output $P_2$ at the emergence terminal of the laser oscillator falls on the power detecting unit 16. A voltage output proportional to the laser output $P_2$ is applied to operational amplifier $Q_1$, amplified therein and then applied to the rotary type potentiometer 35. Accordingly, a voltage output $e_2$ divided by the potentiometer 35 is applied through the resistor $R_7$ to the operational amplifier $Q_4$. The output $\{(e_1+e_2)\times R/R_8\}$ obtained from the operational amplifier $Q_4$ is applied to the motor 34 through the contact $SW_3$ of the off-timer $T_1$. However, as $R_6=R_7=R$, the potentiometer 35 is set to maintain the relation of $e_2=-e_1$ so that when the output obtained from the operational amplifier $Q_3$ is positive, the voltage output $e_2$ is decreased and when the output thereof is negative, the voltage output $e_2$ is increased by means of the motor 34. The value thus set is displayed on a meter M through the operational amplifier $Q_4$. It is possible to produce an indication on the meter M by setting the laser output $P_2$ at the emergence terminal of the laser oscillator to be equal to the laser output $P_1$ at the end section of the manipulator. After a given period of time, after correcting the output of the meter M, has passed after the end section of the manipulator is removed from the measuring hole member 20, the off-timer $T_1$ is operated thereby to close the contact $SW_3$ as a result of which the motor 34 will be unoperable. That is, after correcting the output shown on the meter M, the potentiometer 35 is set at a predetermined position and, accordingly, the corrected output can always be displayed.

What is claimed is:

1. A laser output measuring device for a laser knife with a flexible manipulator comprising:
    a laser oscillator;
    shutter means provided on the optical axis of a laser oscillator;
    a power detecting means for measuring laser output at an emergence port in an end section of said manipulator for a first position of said shutter means and laser output of said laser oscillator for a second position of said shutter means selectively in response to the switching operation of said shutter device;
    a housing including a measuring hole member for fixedly securing said end section of said manipulator in such a manner that the output laser beam from said end section of said manipulator is applied to said power detecting unit for said first position of said shutter means;
    detecting sensor means for detecting whether said end section of said manipulator is inserted into said measuring hole member, said shutter means being coupled to be operated in accordance with an output of said detecting sensor means;
    arithmetic circuit means operating in response to said power detecting means for measuring the laser output of said laser oscillator and converting said laser output of said laser oscillator to a value representative of a laser output at said end section of said manipulator; and
    display means for displaying said laser output at said end section of said manipulator, said display means operating in response to said arithmetic circuit means.

2. The laser output measuring device of claim 1 wherein said shutter means comprises a rotary solenoid and shutter plate mounted on an output shaft of said rotary solenoid, said rotary solenoid being operable to rotate said shutter plate between said first and second positions of said shutter means, said detecting sensor means being coupled to activate said rotary solenoid to rotate said shutter plate to said first position when said end section of said manipulator is positioned in said measuring hole member.

3. The laser output measuring device of claim 1 further comprising mirror means for directing an output of said laser oscillator into said flexible manipulator for said second position of said shutter means.

4. The laser output measuring device of claim 1 wherein said display means comprises an electrical meter.

5. The laser output measuring device of claim 1 wherein said measuring hole member comprises a tightening nut and a retaining member for rotatably securing said tightening nut to said housing.

6. The laser output measuring device of claim 1 wherein said shutter plate is made of light metal having at least a portion thereof coated with a total reflection film.

7. The laser output measuring device of claim 1 wherein said arithmetic circuit means comprises a first operational amplifier having a non-inverting input coupled to an output of said power detecting means; a first switch having a first terminal coupled to an output of said first operational amplifier, said switch being operatively coupled to be operated by said detecting sensor means wherein said first switch is closed when said end section of said manipulator is positioned in said measuring hole member; a second operational amplifier having an inverting input terminal coupled to a second terminal of said first switch; a capacitor coupled to an output of said second operational amplifier for storing a voltage value thereof; a third operational amplifier having a non-inverting input terminal coupled to said capacitor for amplifying said voltage stored by said capacitor; a fourth operational amplifier having an inverting input coupled through a resistor to an output of said third operational amplifier; a potentiometer having a first end terminal coupled to said output of said first operational amplifier, a second end terminal coupled to a ground terminal and a center wiper terminal coupled through a resistor to said non-inverting input of said fourth operational amplifier; a second switch coupled to be operated by said detecting sensor means wherein said second switch is closed when said end section of manipulator is positioned in said measuring hole member; a third switch having a first terminal coupled to an output of said fourth operational amplifier; timer means operating in response to said second switch for closing said third switch a predetermined time after said second switch is closed; and a motor coupled to said third switch wherein said motor is rotated when said third switch is closed, said motor being mechanically coupled to said wiper contact of said potentiometer to position said potentiometer at a position determined by said output of said fourth operational amplifier.

8. The laser output measuring device of claim 7 wherein said display means comprises a fifth operational amplifier having a non-inverting input coupled to said wiper contact of said potentiometer and an electrical meter coupled to an output of said fifth operational amplifier.

* * * * *